United States Patent [19]

Arnold

[11] 4,455,531
[45] Jun. 19, 1984

[54] CONDUCTANCE PROBE FOR DETECTION OF IMMISCIBLE LIQUIDS

[75] Inventor: Orlan M. Arnold, Norwalk, Conn.

[73] Assignee: First Taxing District, Water Department of the City of Norwalk, Connecticut, Norwalk, Conn.

[21] Appl. No.: 280,935

[22] Filed: Jul. 6, 1981

[51] Int. Cl.³ ............................................ G01N 27/02
[52] U.S. Cl. .................................................. 324/448
[58] Field of Search ...................... 324/61 P, 446, 448; 331/65

[56] References Cited

U.S. PATENT DOCUMENTS

| | | | |
|---|---|---|---|
| 1,917,237 | 7/1933 | Barbulesco et al. | 331/65 |
| 2,082,213 | 6/1937 | O'Donnel | 324/448 |
| 2,221,307 | 11/1940 | Christie | 324/448 |
| 2,593,252 | 4/1952 | Booth | 324/446 |
| 2,904,751 | 9/1959 | Parsons | 324/61 P |

Primary Examiner—Michael J. Tokar
Assistant Examiner—Kevin D. O'Shea
Attorney, Agent, or Firm—Bachman and LaPointe

[57] ABSTRACT

This application teaches a probe for detecting immiscible components in an aqueous system, particularly pollutants that contaminate ponds, rivers and aquifers. The probe includes a casing having an open bottom and electrical terminals adjacent the open bottom. Means are provided remote from said casing for detecting change in electrical characteristics, and connecting said remote means to said electrical terminals. The probe registers electrical characteristics on said remote means when said casing is immersed in water, and a variation in said characteristics when said casing passes through a dissimilar fluid.

10 Claims, 2 Drawing Figures

CONDUCTANCE PROBE FOR DETECTION OF IMMISCIBLE LIQUIDS

BACKGROUND OF THE INVENTION

The present invention relates to a probe for detecting media immiscible in aqueous solutions in tanks, ponds, rivers and aquifers wherein the immiscible media has a higher or lower specific gravity than the aqueous solutions.

As is well known, many ponds, rivers and aquifers have become contaminated with a variety of pollutants ranging from harmless to highly toxic substances. These pollutants include water soluble materials, suspended colloidal solids and low water soluble liquids. The immiscible liquids in water form a bi-physical phase system wherein the two or more liquids will separate forming a interfacial boundary. With respect to immiscible liquids having a higher specific gravity than water, the immiscible liquid will form the bottom layer and those having a lower specific gravity than water will form the upper layer.

Examples of common pollutants which are heavier in relation to water include the family of halogen containing organic compounds such as carbon tetrachloride, chloroform, tetrachloroethylene, trichloroethylene, bromo and specific fluoro derivatives and many other substituted organic compounds. Examples of the immiscible liquids of lower specific gravity which form layers on top of the water with an interfacial boundary therebetween include many of the lighter hydrocarbons and derivatives.

Halogenated organic compounds have been entering the ground and water systems from many sources for many years. Many of these compounds are quite stable, do not react to an appreciable degree and do not readily decompose or evaporate. On the other hand, they sink to the bottom of the water or penetrate through porous soil until they reach a continuous confining bottom in a pond, river or aquifer, such as bedrock.

Sources of these halogen containing organic compounds are numerous from industrial manufacture and uses and from domestic applications. Furthermore, many of these materials are quite toxic and represent a serious health hazard. Moreover, despite the fact that there has been heavy emphasis on preventing pollution, it is still well known that a serious pollution problem exists. For example careless introduction of halogen compounds into the earth's surface in the past and during the present is resulting in the accumulation of significant amounts of these materials in our underground water source systems such as our wells and aquifers. There is significant evidence that such contamination is getting considerably worse with time, at least in part due to the fact that the halogen containing organic compounds tend to migrate into the underground water supplies and that the concentrations of these materials are increasing from different sources. The result of all of this has been the closing down of many wells and significant health hazards in many sections of the country.

There is a significant need therefore to be able to determine quickly and inexpensively whether or not underground wells or aquifers are contaminated and how deep and extensive is the contamination layer.

Sampling methods known heretofore are not entirely satisfactory. They are often expensive and time consuming and not very informative as to how deep or extensive the organic contaminant may be. Furthermore, they are often not particularly reliable. The dip stick method is not practical considering the depths of the wells and vertical location of deposits. The pump method of moving large volumes of fluids from a well is not accurate, meaningful or expedient. Optical methods are also not deemed practical and would be difficult and complicated to try to apply.

Accordingly, it is a principal object of the present invention to provide a probe which is efficiently suitable for detecting insoluble aqueous components.

It is a further object of the present invention to develop such a probe which is inexpensive, convenient and expeditious to use.

Further objects and advantages of the present invention will appear hereinbelow.

SUMMARY OF THE INVENTION

In accordance with the present invention, it has now been found that the foregoing objects and advantages may be readily attained.

The probe of the present invention is efficiently suitable for detecting immiscible aqueous components. The probe comprises a casing having an open bottom, electrical terminals inside the casing adjacent the open bottom, means to support the electrical terminals in the casing, means remote from said casing for detecting change in electrical characteristics, electrical connecting means connecting said remote means to said electrical terminals, whereby electrical characteristics register on said remote means when said casing is immersed in water, and a variation in said characteristics when said casing passes through a dissimilar fluid. The casing is preferably a metal tube which is preferably one of the terminals and which can be readily fed through pipes leading to an underground water reservoir. Furthermore, the casing preferably has a closed top and a sealed chamber between the electrical terminal and the closed top. The casing or portions thereof should be of an appropriate metal to provide appropriate electrical readings.

In the preferred embodiment the first electrical terminal is supported centrally in the casing and the second electrical terminal is the casing itself, with both electrically connected to said remote means to register a change in electrical characteristics when water and a dissimilar fluid passes through the open bottom. Preferably, the means for detecting change in electrical characteristics is a means for detecting ohmic impedance change wherein a conductance registers on the remote means when the casing is immersed in water and a variation in said conductance registers when the casing passes through a dissimilar fluid. Naturally, other means may be employed, for example, the means for detecting change in electrical characteristics can include at least one high frequency oscillator controlled by changes of capacitance between the probe electrodes. For example, a fixed frequency and variable frequency oscillator can be provided with the variable frequency oscillator tuned to correspond to the fixed when the probe is immersed in water so that a variation in frequency is not audible until the probe liquid-liquid interface into a dissimilar fluid.

Further features of the device of the present invention will be more readily apparent from the ensuing discussion.

DETAILED DESCRIPTION

Figures 1, 2:
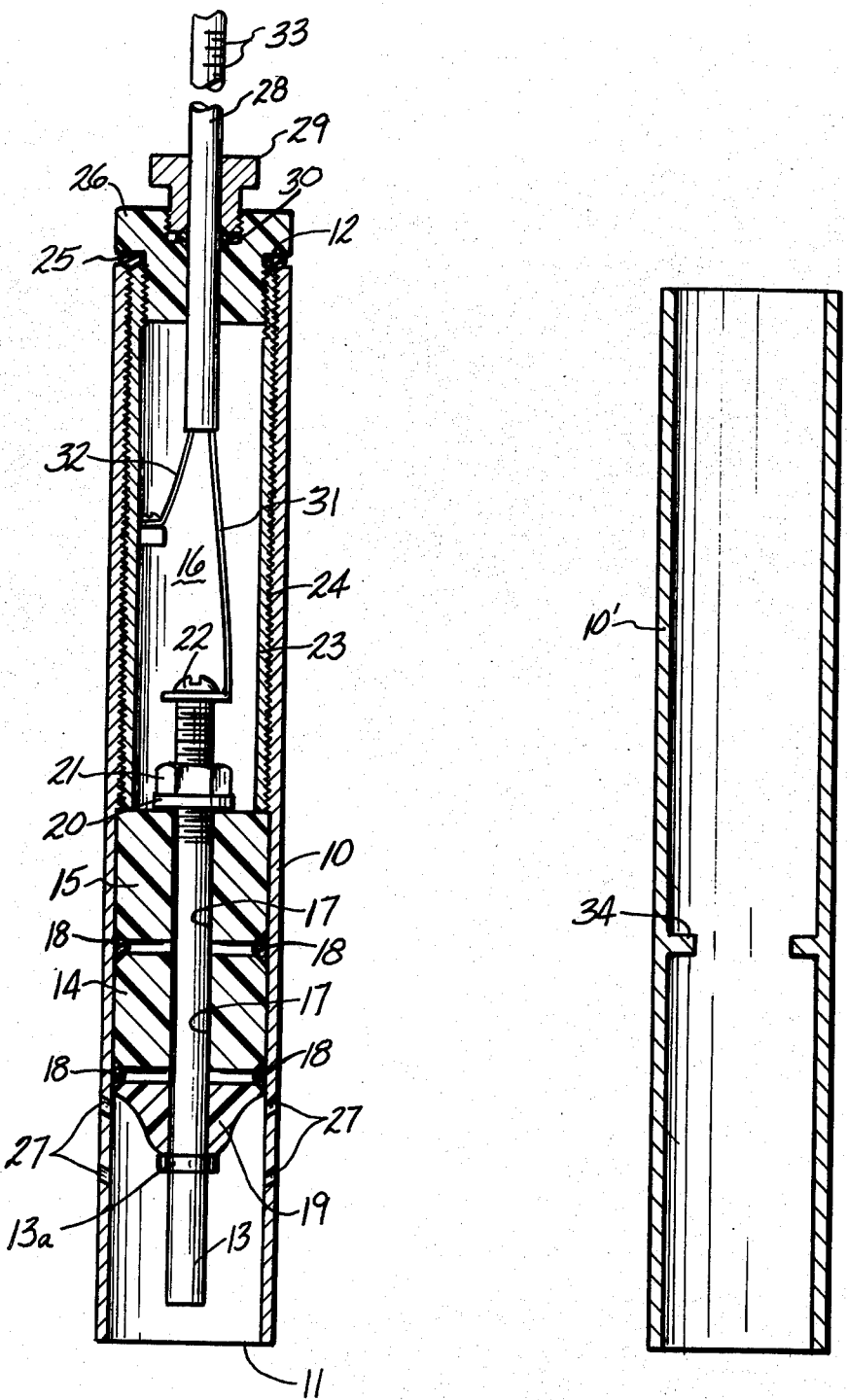
FIG. 1 represents a vertical cross section showing the device of the present invention.
FIG. 2 represents a partly schematic vertical cross section showing a variation in casing configuration.

The device includes an outer shell 10 which is used to house the probe components. The shell is preferably round and tube-like and is preferably made from stainless steel pipe or tubing to resist corrosion. Naturally other appropriate metals can be used. The shell preferably serves as an electrical terminal. Naturally, any particular casing configuration may be suitable, for example for use in a pond or the like.

The casing has an open bottom 11 and a closed top 12. A first electrical terminal 13 is mounted inside the casing adjacent the open bottom, preferably centrally along the axis of the casing. The electrical terminal 13 can be any desired metal and have any desired configuration, preferably a polished stainless steel rod. Naturally, the diameter and length of the electrical terminal may be varied, for example, in order to adjust for the desired ohmic impedance of the liquid in which the probe is immersed.

Electrical terminal 13 is supported in the casing by any desired means. As shown in the drawings, the electrical terminal 13 is supported on one or more co-axially located insulation plugs 14 and 15. In the embodiment shown in FIG. 1, plugs 14 and 15 are tetrafluoroethylene that fit tightly into casing 10 and serve to form a sealed chamber 16 between electrical terminal 13 and closed top 12. Concentric in the plugs are holes 17 so that the electrical terminal can be tightly and snugly fitted therein. O-rings 18 are provided between the tetrafluoroethylene plugs and between insulating cap 19 of electrical terminal 13 to insure a tight seal. In a preferred embodiment cap 19 and plug 14 are a single, unitary piece in order to insure a better water seal. Further sealing means can of course be provided if necessary. The upper end of the electrical terminal is preferably threaded to allow engagement with washer 20 and nut 21 in order to be tightly secured in place and tightly compress plugs 14 and 15. Upper screw means 22 is provided to provide engagement with an electrical connecting means as will be described hereinbelow.

Terminal 13 is provided with integral flange 13a or other suitable securing means to firmly lock the plugs 14 and 15 and cap 19. As shown in FIG. 1, cap 19 is provided with an upwardly sloping surface and is located within outer shell or casing 10. In an alternate embodiment (not shown) the terminal may be a two-piece unit with a screw threaded engagement or the like adjacent the upper portion of the terminal. This will readily permit removal of the terminal for any desired repair of the plugs or O-rings.

In the embodiment shown in the drawings, the case 10 adjacent chamber 16 is formed with an inner sleeve 23 and an outer sleeve 24. The inner sleeve 23 is inserted in the casing from the top, as by a screw-threaded engagement, and extends downwardly to provide an upper rest or stop surface for plug 15. This prevents plug 15 from further upward movement and provides a tight seal. The screw threaded engagement of the inner and outer sleeves is not required. A partially threaded engagement or no threading at all may be employed. The upper end of sleeve 23 is preferably welded to outer sleeve 24 adjacent closed top 12 and may be further provided with an O-ring 25 to insure water tight engagement with threaded cap 26. Preferably, the inner and outer sleeves are welded together adjacent the closed top and a slight depression provided at their interface for locating the O-ring 25 therebetween.

FIG. 2 shows an alternate embodiment avoiding the necessity for an inner sleeve providing that casing 10' has an inner ledge 34 to serve as an upper rest for plug 15. Gaskets or seals should be provided on either side of ledge 34. Alternatively, more than one ledge may be provided and the casing may be in more than one piece.

At a position just below the lower edge of plug 14 one or more holes 27 are provided in casing 10 in order to allow liquids to easily and completely move in and out when the probe is lifted or lowered or when going from one immiscible liquid to the other. The holes can also be provided as small horizontal slits. As shown in FIG. 1, cap 19 is located adjacent holes or apertures 27 and between the first and second electrical terminals.

The structure at the upper end of the probe provides access to chamber 16 so as to attach the wires from marine cable 28 to the casing and to the electrical terminal 13. As indicated hereinabove threaded cap 26 may be tightly screwed into top 12 to provide closing with sealing O-rings 25 therebetween. A step threaded plug 29 may be screwed in place into cap 26 with O-ring 30 between plug 29 and cap 26. As shown, O-ring 30 is preferably provided adjacent cable 28 in a mating depression in cap 26 and plug 29 so as to provide a seal and firmly grasp the exterior of the marine cable. The marine cable 28 is tightly fed into an annular opening in cap 26 and plug 29. The marine cable 28 brings in a first electrical connecting means 31 electrically connected to the first electrical terminal 13 by means of screw 22 and a second electrical connecting means electrically connected to the casing or second electrical terminal. The marine cable is then connected to the remote means for detecting change in electrical characteristics. The marine cable can be of any desired length and can serve as a support in feeding the probe down into wells or aquifers. It provides the electrical wire conductors and circuitry into the probe and can also be calibrated and marked on the cable surface in order to determine the exact depth at which the probe is functioning.

In accordance with the operation of the exemplified device of the present invention, the probe is immersed into an underground well or aquifer. When the probe is in the water phase, the water flows around electrical terminal 13 and out holes 27 reading a sensible conductance on a remote means for detecting ohmic impedance, as an ohm meter. As soon as the probe reaches the contaminant the remote means will detect an impedance change. For example, the chloro compounds referred to hereinabove are insulators and the meter will show an infinity resistance. Also, by calibrating the marine cable as at 33 one can determine the exact depth of the contaminant layer. Means can then be provided to remove the contaminant layer at the exact depth thereof.

Naturally, many variations may be readily practiced within the scope of the present invention. For example, the casing can have a built-in ledge which can be provided to lock in plugs 14 and 15 as shown in FIG. 2. Also, the ledge may provide flat gaskets to be placed on both sides and the respective plugs positioned into their proper places from the two ends. In addition, the casing can be provided in more than one section for easy access to the interior with appropriate sealing means therebetween. Furthermore, the electrical terminal configuration may be varied within the scope of the present invention. It is noted that the electrical terminal is provided above open end 11 in order to prevent damage by contact with solid objects. However, if desired the probe can be movingly situated inside casing 10 so that the electrical terminal can be lowered beneath the level of the casing if desired. Means should then be provided in order to properly orient the electrical terminal in the casing.

It is within the scope of the present invention to provide a variety of methods of detecting or registering the passing of the probe from one immiscible liquid media into another adjacent media. One may provide for the actuation of an ohm meter. The differences in conductance of one immiscible liquid between the exposed electrodes of the probe with the conductance of another liquid can be visually followed with a sensitive ohm meter. Alternatively, the change in brightness of an electric light signalling device or bulb in an electrically energized circuit containing the probe electrodes immersed in succession in immiscible liquids of different electrical conductances can visually show the change. Still further, a bell or buzzer in the electrically energized circuit containing the probe electrodes immersed in succession in two immiscible liquids of different conductivities will alert by sound the transition from one media to another. Still further, by electrical transmission of signal through the marine cable of changes in high frequency oscillation controlled by changes of impedance between the probe electrodes can serve as the alerting means to show the presence of a high dielectric medium or a low dielectric medium.

Thus, the electrical detection with the probe of the present invention is readily achieved and may operate on the basis of change of ohmic resistances between the probe electrodes immersed in different liquids. The changes in resistances may be signalled by changes in ohm meter readings or other means discussed hereinabove. Naturally, the probe of the present invention can if desired be used in a stationary position with changing levels of the meniscus boundary with time. When the meniscus reaches a certain elevation or descends to a specific low level the probe can alert with circuited signals the reaching of a prescribed liquid-liquid interface level. Alternatively, one can readily adapt the probe through electrical circuits to open or close a valve to control flow out of or into one of the immiscible liquids. Numerous other variations may readily be devised.

It is to be understood that the invention is not limited to the illustrations described and shown herein, which are deemed to be merely illustrative of the best modes of carrying out the invention, and which are susceptible of modification of form, size, arrangement of parts and details of operation. The invention rather is intended to encompass all such modifications which are within its spirit and scope as defined by the claims.

What is claimed is:

1. A probe for detecting immiscible components in an aqueous system which comprises a casing having an open bottom and a closed top, a first electrical terminal and second electrical terminal spaced from each other inside the casing adjacent the open bottom, a sealed chamber between the first electrical terminal and closed top, means between said first electrical terminal and sealed chamber to seal said chamber from water, means within said casing for retaining said sealing means, means to support the terminals in the casing, means remote from the casing for detecting change in electrical characteristics, a first electrical connecting means connecting said remote means to said first electrical terminal and second electrical connecting means connecting said remote means to said second electrical terminal, means in said casing adjacent said first electrical terminal including a plurality of apertures in the casing to provide a continuous flow of fluid adjacent said first electrical terminal, means having an upwardly sloping surface within said casing adjacent said apertures between said first and second electrical terminals, whereby said remote means registers electrical characteristics when said casing is immersed in water and a variation in said characteristics registers on said remote means when said casing passes through a dissimilar fluid.

2. A probe according to claim 1 wherein said means for detecting change in electrical characteristics is a means for detecting ohmic impedance change.

3. A probe according to claim 1 wherein said means for detecting change in electrical characteristics includes at least one high frequency oscillator controlled by changes of capacitance between the probe electrodes.

4. A probe according to claim 1 wherein said casing is a metal tube.

5. A probe according to claim 4 wherein said second electrical terminal is the casing.

6. A probe according to claim 1 wherein said first and second electrical connecting means enter the casing through said closed top, said first electrical connecting means is electrically connected to said first electrical terminal through said sealing means, and said second electrical connecting means is connected to said casing inside said sealed chamber.

7. A probe according to claim 5 wherein the first electrical terminal is supported centrally in said casing.

8. A probe according to claim 5 wherein said remote means is connected to said first electrical terminal and casing by means of a calibrated marine cable.

9. A probe according to claim 1 wherein said casing is provided wih an inner sleeve.

10. A probe according to claim 1 wherein said closed top is provided with means for access to said sealed chamber.

* * * * *